United States Patent [19]

Rilbe

[11] 4,217,193
[45] Aug. 12, 1980

[54] METHOD AND APPARATUS FOR ISOELECTRIC FOCUSING WITHOUT USE OF CARRIER AMPHOLYTES

[75] Inventor: Harry Rilbe, Göthenburg, Sweden

[73] Assignee: Ingenjörsfirman Gradient Birgit Och Harry Rilbe, Sweden

[21] Appl. No.: 908,639

[22] Filed: May 23, 1978

[30] Foreign Application Priority Data

Jun. 2, 1977 [SE] Sweden ............................. 7706359

[51] Int. Cl.² ........................................... G01N 27/28
[52] U.S. Cl. ............................. 204/180 G; 204/180 R; 204/180 P; 204/299 R; 204/301
[58] Field of Search ........... 204/180 R, 180 G, 180 S, 204/180 P, 299 R, 301

[56] References Cited

U.S. PATENT DOCUMENTS

| | | | |
|---|---|---|---|
| 4,048,049 | 9/1977 | Hoefer | 204/299 R |
| 4,049,534 | 9/1977 | Posner | 204/299 R |
| 4,088,561 | 5/1978 | Anderson | 204/180 G X |

*Primary Examiner*—Arthur C. Prescott
*Attorney, Agent, or Firm*—Burns, Doane, Swecker & Mathis

[57] ABSTRACT

An ampholyte is purified by being enclosed in a capillary system forming a convection-free zone, direct current being passed through said zone. The electrolyte contains at least one buffering ion constituent. Electrolyte zones are created on both sides of said convection-free zone. Convection is created in said electrolyte zones to homogenize the electrolyte in said zones. Two equal liquid flows of reverse directions are created between said two homogenized electrolyte zones.

16 Claims, 6 Drawing Figures

METHOD AND APPARATUS FOR ISOELECTRIC FOCUSING WITHOUT USE OF CARRIER AMPHOLYTES

Steady state electrolysis is understood as an electrolysis process performed between unchangeable electrodes through an electrolytic conductor, convection-free at least in some portions, for such a long time that all present electrolytes reach time-independent concentrations in all parts of the electrolyzer. The steady state is characterized by a dynamic equilibrium between mass transport due to ionic migration and mass transport due to diffusion. A strict steady state implies absence of material losses due to anodic oxidation, cathodic reduction, evaporation, precipitation, etc. Evolution of hydrogen at the cathode and of oxygen at the anode, however, cannot possibly be avoided, but the sole effect thereof is a slow consumption of water.

Since acids are attracted to the anode and bases to the cathode on electrolysis, a monotonously increasing pH from anode to cathode will develop in the convection-free electrolytic conductor. Such a pH gradient is useful for analysis and separation of ampholytes, especially proteins, since they are positively charged in acidic and negatively charged in alkaline media. They are thus repelled by both electrodes and concentrate to the spot in the electrolytic conductor where the local pH coincides with the isoelectric point of the ampholyte. This process is called isoelectric focusing, and its success depends entirely on the satisfaction of the three conditions (1) that the pH gradient is stable in time; (2) that nowhere an electrolyte vacuum develops which tends to quench the current and/or give rise to local overheating; (3) that the pH gradient $d(pH)/dx$ has a low value in the pH region of interest in the actual separation. In general, there are no difficulties in satisfying the first condition in steady state electrolysis in a convection-free medium. Yet it is well known that pH gradients in gel media deteriorate strongly on uncalled-for prolongation. The last two conditions can be satisfied if one chooses so-called carrier ampholytes as electrolyte system and essentially excludes salts. Carrier ampholytes are defined as ampholytes of relatively low molecular weight and having conductance as well as buffer capacity in the isoelectric state. For establishing suitable pH gradients it is necessary to have access to a great number of carrier ampholytes with isoelectric points well distributed along the pH scale. Quite a number of other requirements, related to protein analysis, must also be satisfied by well functioning carrier ampholytes.

A sufficient number of single carrier ampholytes are not available on the chemical market. Therefore the specially produced preparations Ampholine® and Servalyt® are almost the only ones useful for this purpose. They satisfy all demands that reasonably can be put on carrier ampholytes, and isoelectric focusing with use of Ampholine® or Servalyt® has therefore been developed into a very useful and generally applied analysis and separation method for proteins. Its resolving power is without competition, which is due to the fact that the electric focusing force balances the spreading tendency of diffusion. A summary of the theory for isoelectric focusing in the presence of carrier ampholytes has been given by the inventor in Ann. N.Y. Acad. Sci. 209 (1973), pp. 11-22, and in the same volume numerous descriptions of various experimental arrangements and of applications can also be found.

The high price of Ampholine® and Servalyt® is a hampering factor in the general use of isoelectric focusing. This is especially the case in situations where it is desired to use the method preparatively on greater amounts of material, requiring proportionally large amounts of carrier ampholytes.

Another repressing factor is the fact that the electrolysis gives rise to a drastic decrease of the ionic strength and consequently to very low solubilities of proteins with the character of globulins, which will precipitate at their isoelectric points, where they exhibit solubility minima. Many globulins precipitate even irreversibly on removal of salts in the isoelectric state, that is, they are denatured and cannot be brought back to their native state by addition of salts and adjustment of pH to a normal value.

The possibility of successful isoelectric focusing is evidently altogether equivalent with the possibility of producing suitable pH courses in electrolytic conductors passed by an electric current. The present invention aims at realization of procedure and apparatus for preparation of pH courses, stable on passing of a direct current, within a convection-free portion of an electrolytic conductor with the aid of ordinary buffer substances, thus without carrier ampholytes. These pH gradients can have considerable salt concentrations and conductivities, and their form and extension can be varied and adapted to various analysis and separation problems of current interest within the frame of isoelectric focusing.

The principle of the invention is evident from the following consideration. On electrolysis of an ordinary buffer solution, e.g. an acetate buffer consisting of a mixture of sodium acetate and acetic acid, the electric current will bring about a complete separation of acid and base. In the steady state, the acetic acid concentration will decrease monotonously from the anode towards the center of the apparatus, whereas the sodium hydroxide concentration will decrease monotonously from the cathode towards the center. An electrolyte vacuum will thus develop at some spot in the central part of the apparatus, and there the very low conductivity will tend to quench the current and/or give rise to local over-heating. To avoid that, one can introduce homogenization at that spot, thereby arranging a certain remixing of acid and base and maintaining a higher conductivity in the critical region. However, the fact remains that the buffer solution is electrolyzed away and that the resulting pH course becomes very unfavourable and hardly useful for anything.

According to the present invention, two equal and constant liquid flows in opposite directions are arranged, while a constant current is flowing through the electrolyzer, between two portions of the electrolytic conductor which are incessantly homogenized by convection, e.g. by active stirring, said homogenized portions being situated on either side of the convection-free portion in which the separation takes place. The liquid flows transport a more acid solution to a less acid region of the electrolytic conductor while a less acid solution is transported to a more acid region. Alternatively, both current and liquid flows can be allowed to vary provided that their ratio is kept constant. The process shall be allowed to continue until a steady state develops, characterized by concentrations and physical properties that no longer change in any part of the electrolysis apparatus.

Within the region between said two homogenized portions of the electrolyzer, then, as much of the anionic constituent is transported in the direction to the cathode as the amount migrating electrophoretically towards the anode, and likewise, as much of the cationic constituent is pumped towards the anode as the amount migrating electrophoretically towards the cathode. Both ionic species will therefore circulate between the two homogenized portions, the buffer salt cannot disappear within this region, but a certain salt concentration can be maintained. Because the electric current all the time continues to try to separate acid and base, pH will increase in the direction of the current, but, since both buffer components are present everywhere within the convection-free portion, pH will be tied to the buffer range of the weak acid. The pH gradient will thus get a comparatively low value, favouring separation with good resolution. It is a known fact that the resolving power in isoelectric focusing is improved on reduction of the pH gradient.

It is possible to influence the pH course though variation of the ratio between electric current and liquid flow. At relatively small liquid flows one gets a relatively steep pH course and a relatively great pH range. If the liquid flows are increased relatively to the current, one obtains more shallow pH courses comprising a narrower pH range.

It is thus evident that production of a stable pH course according to this invention requires at least one convection-free portion of the electrolytic conductor and at least two convectively homogenized portions between which two equal liquid flows in opposite directions can be arranged with the aid of suitable system for liquid transport.

According to a special procedure and a special arrangement for practising this invention. The liquid exchange is arranged between anolyte and catholyte. Vivid evolution of oxygen and hydrogen normally takes place in these solutions. Since these gases cause convection, homogenization by other means can possibly be regarded as superfluous. Liquid exchange between anolyte and catholyte has the advantage that the resulting pH course can be calculated relatively easily if certain simplifying assumptions can be regarded as satisfied. In the general case such calculations cannot be performed, but qualitative predictions concerning the pH course can always be made on the basis of pH values and concentrations of the weak protolytes used. For the rest one must use empirical methods for the choice of suitable protolyte composition for every particular separation problem.

Figure 1:
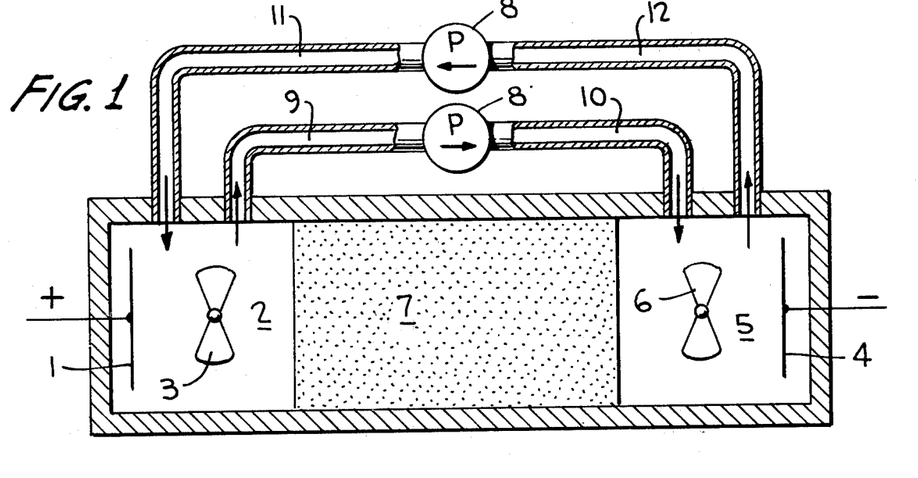
FIG. 1 is a side view in section of a first embodiment of an electrolyzer for mixing anolyte and catholyte in accordance with the present invention.

The principles of the invention is also illustrated in the block scheme in FIG. 1 for the case of liquid exchange between anolyte and catholyte. There (1) is the anode, (2) is the anode compartment containing the anolyte, homogenized by the stirrer (3), (4) is the cathode, (5) is the cathode compartment containing the catholyte, homogenized by the stirrer (6), (7) is the convection-free portion of the electrolytic conductor, in which the desired pH course develops in the steady state, (8) is the pumping arrangement producing two equal and oppositely directed liquid flows, and (9), (10), (11) and (12) are the four liquid ducts outside the electrolyzer, all with the same liquid flow. Within the electrolyzer there is no net liquid flow. Experimental experience has shown that the two liquid flows must be exactly equal.

In the simplest case the buffer solution consists of one single salt, one of its ion constituents buffering within the desired pH range, together with an excess of the weak protolyte, acid or base, corresponding to said ion constituent. For instance, if a pH gradient in the region 3-6 is desired, it is suitable to prepare a buffer solution consisting of sodium acetate and acetic acid. If the desired pH region is on the alkaline side of the neutral point, one can choose an amine with a pH value lying within the proper pH range, partially neutralize it with sulphuric acid, and use the resulting buffer solution as electrolyte medium. With use of one single buffering ion constituent, a pH range not greater than 2.5-3 pH units can be mastered with this technique, and according to available theory this is accomplished by using a flow rate V a little bit greater than $Ti/2FC$, where i is the electric current, F is Faraday's constant, C is the initial concentration and T the transference number of the ion constituent without buffering action. If a too low flow rate is applied, one of the buffer components will disappear altogether from one of the homogenized portions between which the liquid exchange takes place. For a certain optimal excess of the buffering component, this occurs simultaneously for both components, and the critical flow rate given above refers to this optimal excess. If the flow rate is lower than the critical value, the pH range increases drastically, but at the same time the buffering action disappears in the outer regions of the apparatus, and the pH course becomes unfavorable. If the flow rate is appreciably greater than the critical value, the pH region becomes smaller, and the pH course becomes shallower. This is favorable for fine separation within a narrow pH interval.

If one desires to perform isoelectric focusing within a wider pH range according to this invention, one can use a salt in which both ion constituents have a buffering action. The best result is then obtained if the buffer range of the cation lies about 3 pH units higher than that of the anion since in that case the two buffer regions simply add to each other, and one obtains a very suitable pH course within a pH range of the double extension. A good example of this technique is the use of imidazol hydroacetate, which can be prepared by mixing equivalent amounts of imidazol and acetic acid. The cationic pH lies at pH 7, the anionic one at 4.7. Hence stationary electrolysis can be expected to give a very suitable pH gradient in the region between pH 3.2 and 8.5. No excess of imidazol or acetic acid is necessary, but if such an excess is nevertheless applied, the useful pH range will get a shift upwards or downwards. The pH courses obtainable through electrolysis of salts with two buffering ion constituents are still open to calculation, which is an advantage.

It is also possible to use buffer systems with more than one buffering anionic constituent and buffer systems with more than one buffering cationic constituent. Calculation of the expected pH course is then hardly possible, but qualitative predictions can be made, and empirical methodology is always available in order to arrive at suitable buffer systems for special purposes.

As a common rule one can state that monovalent buffering ion constituents should be preferred. As far as possible, one should also choose ion constituents which are not affected by losses in the process through anodic oxidation, cathodic reduction, or evaporation. Thus ammonia is far too volatile, and aniline coming into the anodic compartment will give rise to black dyestuffs. Halides must be excluded since they are oxidized to free halogens at the anode.

Difficulties may arise in finding buffering ion constituents completely resistant against anodic oxidation. Since such processes are favored by a high current density, as large electrodes as possible should be used. If still there is reason to believe that too great losses occur at the anode of an ion constituent susceptible to oxidation, it is possible to use as anolyte a dilute solution of sulphuric acid or phosphoric acid, which are very stable against oxidation, and to allow the pumping system to work between a homogenized portion at a distance from the anode and a homogenized portion at or near the cathode.

It is essential that only the buffer substances are transported through the pumping system outside the electrolyzer. Thus, if the pH gradient is used for separation of protein systems containing components with isoelectric points lying outside the pH range in the apparatus, these components must be prevented from migrating into the homogenized portions. Most simply, this is achieved by insertion of protein-tight membranes between the two homogenized portions and the central part of the electrolysis apparatus.

The invention also comprises apparatus for performing isoelectric focusing in pH gradients produced according to the invention. Such an apparatus is characterized by a combination of an already known apparatus for isoelectric focusing with devices for homogenization of at least two portions of the electrolyzer and with a device for liquid transport accomplishing two equal liquid flows in opposite directions between said two homogenized portions.

As already mentioned, the two liquid flows in opposite directions must be very exactly equal. If this condition is not satisfied, and if the convection-free portion has a low resistance to flow, there will be a net liquid flow through the latter portion equal to the difference between the two external flows. Experiments have shown that in such a case a constant pH develops in the greater part of the apparatus, whereas a steep pH course is obtained in the remaining, smaller part. Such a pH course is completely useless. If the convection-free portion has a great resistance to flow, there will be an incessant net liquid transport from one homogenized portion to the other, which has inacceptable consequences. However, this can be avoided through devices for automatic reflux from the homogenized portion tending to overflow to the one tending to drain. This can easily be accomplished, for instance with the aid of a siphon from which liquid drips down into the homogenized portion tending to drain. In such an arrangement, no electric current can pass through the siphon. One can also use a duct completely filled with liquid between the two homogenized portions if this duct is sufficiently long and narrow in order to make the current flowing through quite negligible in relation to the main current.

If this line of thought is pursued, it leads to the logical consequence that a dual pump, or two single pumps, are more than what is required for realization of the invention in the case of a great resistance to flow in the convection-free portion. It is sufficient with one pump with a constant rate of flow, or with a rate of flow governed to proportionality to the current, in combination with a device for automatic reflux between the two homogenized portions of the apparatus. This arrangement is through its simplicity so much to be preferred that there are very strong reasons to introduce a flow-tight membrane, e.g. a sheet of cellophane or animal tissue, somewhere in an apparatus with low resistance to flow in the convection-free portion in order to make it possible to use the principle with automatic reflux. The membrane in question should be inserted at a place minimizing the risk of an electroösmotic flow. Since most membranes have an electronegative character, this means that the membrane should be inserted at the acidic homogenized portion, on the side toward the center of the apparatus.

Especially at work in alkaline media, it may be difficult to find a membrane sufficiently flow-tight and with a sufficiently small electroösmotic effect. Then it becomes necessary to construct a liquid transport device giving exactly equal flows in opposite directions. No existing pumps operate with the great exactitude required in this connection. This problem can be solved by using a device shown in FIG. 2.

Figure 2:
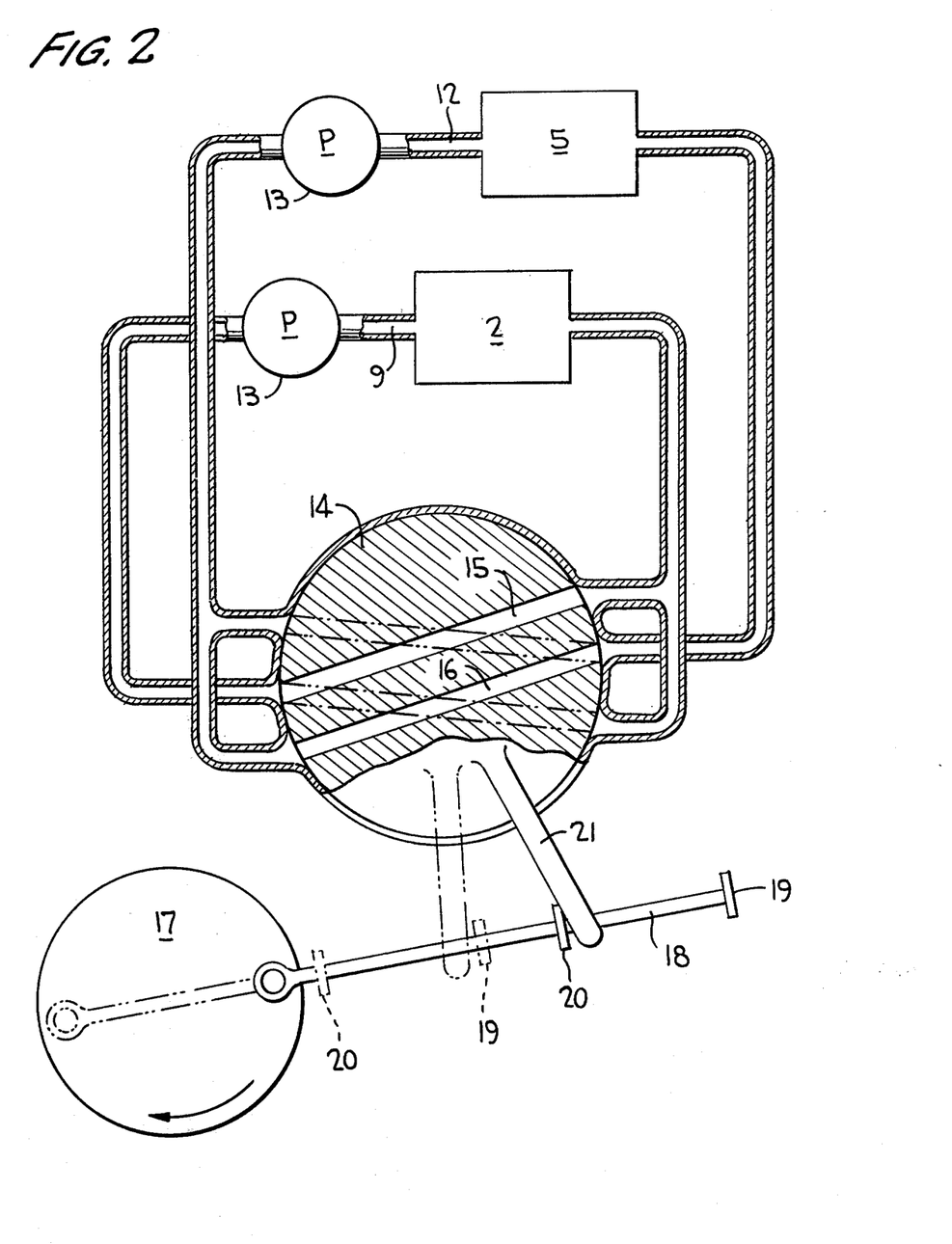
FIG. 2 is a side view in section of a second embodiment of the invention in which the anolyte and catholyte are mixed by means of a stopcock.

In the liquid duct (9), the anode compartment (2) and the membrane pump (13) are coupled in series, and similarly the cathode compartment (5) and another membrane pump (13) are coupled in series in the liquid duct (12). These pumps operate at speeds much greater than the desired liquid exchange between the two homogenized portions of the apparatus. Both flows go by way of the two-way stop-cock (14) back to the compartment from which they came. As long as the stopcock (14) is not turned, therefore, no liquid exchange occurs between anolyte and catholyte; the pumps (13) act exclusively as stirrers for the contents of the respective compartments.

In the position of the stop-cock that is indicated by the full-drawn lines, the upper plug channel (15) is filled with anolyte, the lower plug channel (16) with catholyte. The stop-cock plug is now brought to change between the two orientations indicated by full-drawn and dashed lines. This is achieved with the aid of the eccentric disc (17) rotating at a constant speed, the rod (18) with two stops (19) and (20), and the lever arm (21) of the stop-cock plug, worked upon by said stops. Due to this construction, the stop-cock will be open during a comparatively large part of a turn of the eccentric disc. In the dashed orientation of the stop-cock plug, the upper channel (15) becomes filled with catholyte, the lower one (16) with anolyte, but even in this orientation both liquid flows go back to the compartment from which they came.

The liquid exchange between anolyte and catholyte is in this way limited to the very alternation between the two end positions of the stop-cock. The latter acts as a liquid commutator. The rate of liquid exchange is determined by the volumes of the two plug channels and by the frequency of the stop-cock movements. The rate of flow through the pumps does not at all influence the rate of liquid exchange between the electrode compartments. Nor does a possible difference between the volumes of the plug channels play any role since every channel is filled alternatingly with anolyte and catholyte.

What has been said above about anode and cathode compartments and about anolyte and catholyte remains valid for any other compartments and their contents which can be chosen for continuous liquid exchange according to the principles of this invention.

Within conventional isoelectric focusing, four different types of apparatus are of dominating importance. A brief description of them will be given here, and in connection therewith it will be discussed how they can be adapted to functioning according to the principles of the present invention by way of additional devices.

The first type of apparatus comprises a multitude of cooled and homogenized compartments separated by a multitude of membranes, essentially perpendicular to the current direction and with a porosity sufficiently low to make them essentially convection-free, but sufficiently high to leave free passage to proteins. Liquid exchange according to this invention can then be arranged between any pair of compartments. For obvious reasons these compartments are chosen at a rather great mutual distance. The electrode compartments can also be chosen for mutual liquid exchange unless anodic oxidation, cathodic reduction, or the gas evolution in them make this choice unsuitable. The homogenized compartments between which the liquid exchange is arranged can be delimited against the central part of the apparatus by protein-tight membranes if so deemed necessary.

The second type of apparatus comprises two electrode compartments and between them a horizontal, cooled, and electrically insulating plate suitable for application of a moistened layer of a capillary system in electrolytic connection with the electrode compartments. This type of apparatus can be adapted to the present invention by introduction of effective homogenization in the electrode compartments and continuous liquid exchange between them. If the electrode compartments are unsuitable for this purpose, two additional compartments may be introduced between them and the capillary system. Homogenization and liquid exchange are then arranged in and between these extra compartments.

The third type of apparatus comprises two electrode compartments at different levels and between them one or more vertical, cooled, and electrically insulating tubes suitable for filling with a moistened capillary system in electrolytic connection with the electrode compartments. The capillary system is often made up of a polyacrylamide gel having such a great flow resistance that the overpressure in the upper electrode compartment is incapable of giving rise to any measurable liquid flow through the gel. However, the tube or tubes can also be filled with a more porous capillary system, and liquid flow through them then has to be prevented by elimination of the pressure difference between the electrode compartments, most simply by attaching an ascending tube to the lower electrode compartment, this tube being filled with liquid to the same level as in the upper electrode compartment. This type of apparatus can be adapted to the present invention by arranging effective homogenization in the electrode compartments and continuous liquid exchange between them. If the electrode compartments are unsuitable for this purpose, two additional compartments can be introduced between them and the convection-free vertical tubes. Homogenization and liquid exchange is then arranged in and between these extra compartments.

The fourth type of apparatus comprises a so-called density gradient column, that is, a column in which the density increases downwards due to a concentration gradient of a heavy non-electrolyte, usually sucrose. It also comprises a gas-escape tube, also vertical and communicating with the column at the bottom, with one of the electrodes, the other electrode being situated at the top of the column. This type of apparatus can only with great difficulties be adapted to the present invention.

In the following, with reference to FIGS. 3 and 4, some possible apparatus constructions according to the invention are shown as examples, but not in any limiting sense. In addition, FIG. 1, used to explain the principle, can also be seen as a description of an electrolyzer in which the convection-free portion (7) is a horizontal layer of a gel or powder paste resting on a plane, cooled support. The liquid transport arrangement (8) can be a combination of two membrane pumps and a liquid commutator according to FIG. 2, the stirrers (3 and 6) in anolyte and catholyte then becoming superfluous. The device (8) can also be one single peristaltic pump transporting anolyte over to the cathode compartment at a constant speed, the liquid ducts (11 and 12) not passing through any pump, but directly united serving as a reflux tube for automatic transport of catholyte to the anode compartment (2).

Figure 3:
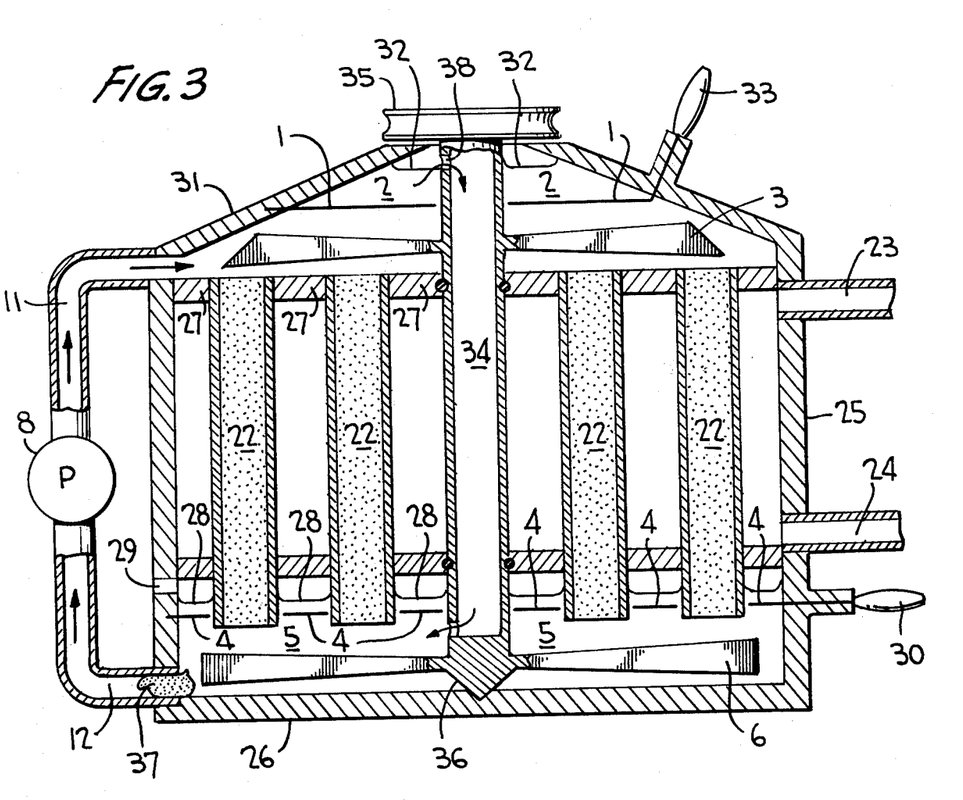
FIG. 3 is a side view in section of a third embodiment of the invention in which the anolyte and catholyte are disposed at different vertical levels.

In the apparatus construction according to FIG. 3, the convection-free portion (7) of the electrolyzer consists of columns (22) containing a flow-tight gel or a powder packing resting upon gel plugs at the bottom of vertical tubes connecting the upper anode compartment (2) with the lower cathode compartment (5). In the apparatus according to the figure there are a number of parallel-coupled columns for simultaneous isoelectric analysis of several samples. All of them are cooled by a refrigerating medium going in and out through the side tubes (23 and 24) to and from the refrigerating chamber bounded by the cylindrical wall (25), the bottom plate (26), and the roof plate (27). In the cathode compartment the catholyte has its meniscus at (28) above the cathode (4) and the stirring blade (6). Cathodically evolved hydrogen escapes through the hole (29). The cathode (4) is fastened to the cylindrical internal wall of the cathode compartment (5) at some spots round the periphery, and at one point it is connected to the external banana plug (30) by way of a wire going through said wall. In the anode compartment (2) with a conical ceiling (31), the anolyte has its meniscus at (32) above the anode (1) and the stirring blade (3). The anode (1) is fastened to the conical ceiling (31) of the anode compartment (2) at some spots round the periphery, and at one point it is connected to the external banana plug (33) by way of a wire going through the roof. Both stirring blades (3 and 6) are fastened to the same vertical axis shaped as a tube (34), at the top equipped with a pulley (35) and at the bottom with a tip (36) fitting into a conical recess in the bottom plate of the cathode compartment (5). The peristaltic pump (8) is connected to the catholyte via the tube (12) and with the anolyte via the tube (11). The cotton plug (37) prevents the passage of hydrogen bubbles. Automatic reflux of anolyte to the cathode compartment (5) takes place through the hole (38) in the tube-shaped stirring axis (34). This hole is situated far up in the anode compartment in order to reduce the area of the anolyte meniscus (32).

Figure 4:
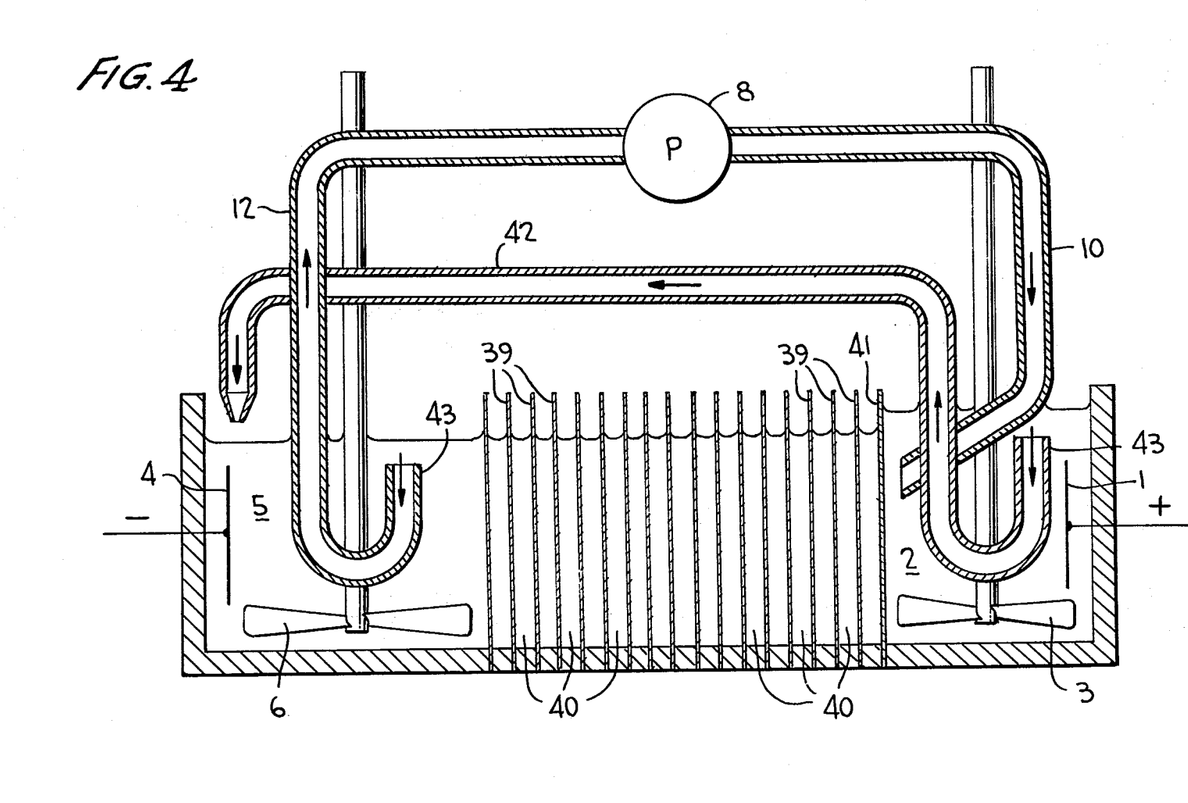
FIG. 4 is a side view in section of a fourth multi-compartmented embodiment of the invention.

In the apparatus construction according to FIG. 4, the convection-free portion (7) of the electrolysis apparatus consists of a number of membranes (39) stretched perpendicular to the current direction and separating a number of compartments (40), preferably both stirred and cooled. The membranes (39) have to be permeable to proteins and can be made of filter paper. The membrane 41 bounding the anode compartment (2), however, should be very tight and not allow any liquid transport due to the low overpressures that may develop. Anolyte and catholyte are homogenized by the stirrers (3 and 6). The peristaltic pump (8) transports catholyte to the anode compartment (2) through the duct (10 and 12), and automatic reflux of anolyte to the cathode compartment (5) is effected by the siphon (42), which starts functioning when the level difference between the anolyte miniscus and the tip of the siphon has reached a certain value. The tube (12) in the catholyte, as well as the siphon (42) in the anolyte, have inverted tube ends (43) in order to prevent gas bubbles from the electrodes to accompany the liquid stream.

The invention has been tested in a multi-compartment apparatus according to FIG. 4, yet without the tight membrane (41) and without a siphon for automatic reflux. Two exactly equal liquid flows in opposite directions were instead realized with the aid of the device according to FIG. 2.

Figure 5:
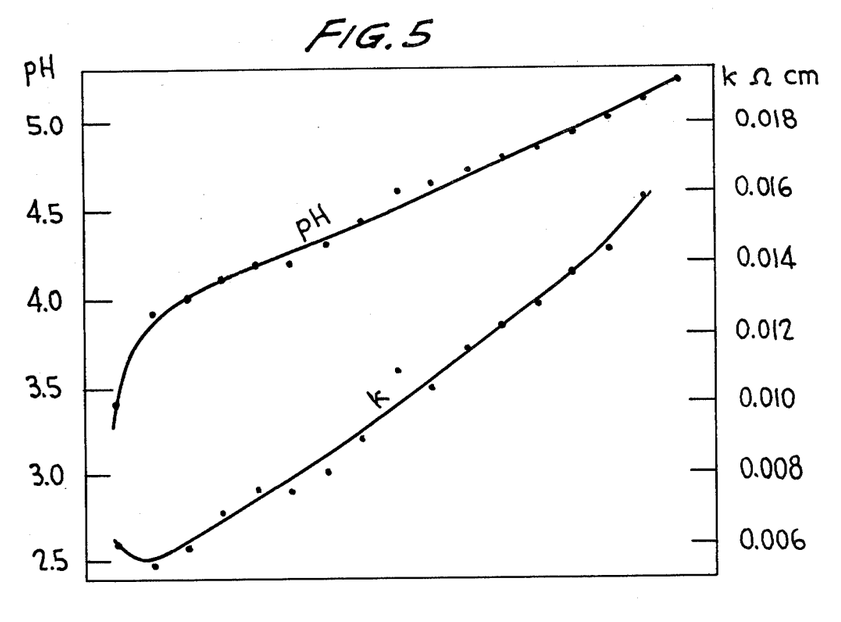
FIG. 5 is a graph illustrating pH and conductivity vs. time for a first electrolyte in a multi-compartmented mixing apparatus.

In one experiment an acetate buffer of the composition 0.0775 M sodium acetate, 0.110 M acetic acid, and 0.010 M sodium sulphate was used. Liquid exchange was arranged between anolyte and catholyte. The current was 1.0 A, and the pumping speed was 2.82 cm$^3$ per minute. The number of compartments was 17, and the total volume about 1 liter. Each compartment had facilities for cooling as well as stirring. After less than 24 hours the steady state had been established, and thereafter one had in the electrolysis apparatus an unchanging pH course as shown in FIG. 5. The useful pH gradient thus comprised 1.3 pH units in this case, between pH 3.9 and 5.2. The conductivity course is also shown in FIG. 5. The conductivity is lowest in the anolyte and is about 3 times as high in the catholyte. The field strength thus varies with a factor of 3 within the electrolyzer. This is unfavorable, but in conventional isoelectric focusing in the presence of carrier ampholytes the field strength varies much more than that. The method according to the invention thus involves an improvement even in this respect.

Figure 6:
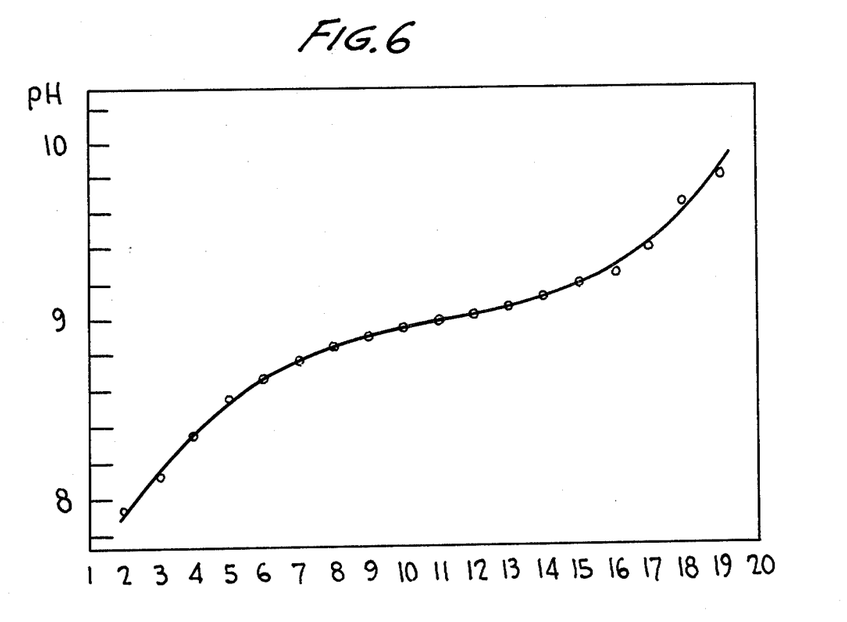
FIG. 6 is a graph illustrating pH vs. time for a second electrolyte in a multi-compartmented mixing apparatus.

In another experiment a borate buffer of the composition 0.1M borax and 0.1 M boric acid was electrolyzed with a current of 0.6 A and a liquid flow of 3.09 cm$^3$/minute. This experiment was carried out in a 20-compartment apparatus in which each compartment held 25 cm$^3$. The liquid exchange was effected between the compartments next to the electrode compartments. This experiment gave a stable pH course according to FIG. 6.

What I claim is:

1. A method for the purification of ampholytes through isoelectric focusing, comprising the steps of:
    providing an electolytic conductor containing at least one buffering ion constituent;
    creating in said electrolytic conductor at least one convection-free zone containing a capillary system;
    adding ampholytes to be purified to said convection-free zone;
    creating convection zones in said electrolytic conductor on opposite sides of said convection-free zone;
    maintaining a convection in each of said convection zones to homogenize the electrolyte in each of said convection zones;
    passing direct electric current through the convection-free zone to create in the electrolyte in said convection-free zone a steady pH gradient in the direction of the current; and
    creating two equal flows of electrolyte in opposite directions between said two convection zones, the rate of each of said flows of electrolyte being greater than Ti/2FC but no greater than a flow rate necessary to maintain a predetermined pH gradient between the two convection zones, wherein
    T is the transference number of the ion constituent without buffering,
    i is the magnitude of the electric current,
    F is Faraday's constant, and
    C is the initial concentration of the ion constituent.

2. Procedure according to claim 1, characterized in that the homogenized portions of the electrolytic conductor are the anolyte and catholyte and in that the equal liquid flows are arranged between these portions.

3. Procedure according to claim 1, characterized in that the electrolytic conductor is composed of a number of compartments where continuous homogenization is effected, the compartments being separated by a number of membranes, essentially perpendicular to the current direction and with a porosity sufficiently small to make them convection-free, but sufficiently great to give free passage to proteins.

4. Procedure according to claim 1, characterized in that the convection-free portion of the electrolytic conductor is a gel.

5. Procedure according to claim 1, characterized in that the convection-free portion of the electrolytic conductor is a powder packing.

6. Procedure according to claim 1, characterized in that the electrolyte system contains a salt of a strong base and a weak acid and an excess of the weak acid.

7. Procedure according to claim 1, characterized in that the electrolyte system contains a salt of a strong acid and a weak base together with an excess of the weak base.

8. Procedure according to claim 1, characterized in that the electrolyte system contains a salt of a weak base and a weak acid.

9. Procedure according to claim 1, characterized in that the electrolyte system, for protection of an oxidizable ion constituent against anodic oxidation, contains at least one strong acid resistant against anodic oxidation, and in that no liquid exchange is effected between the anolyte and any other part of the electrolytic conductor.

10. Procedure according to claim 1, characterized in that the two homogenized portions between which liquid exchange is effected are delimited against the convection-free portion by membranes which are impermeable to the ampholytes under separation.

11. Apparatus for use in the purification of ampholytes through isoelectric focusing, comprising:
    means for housing an electrolytic solution and defining a convection free capillary system in which separation of ampholytes takes place;

first and second compartments in fluid communication with opposite sides of said convection-free capillary system and defining first and second convection zones;

an electrode disposed within each of said first and second convection zones;

means for homogenizing an electrolytic conductor contained in each of said first and second convection zones;

means defining two paths of fluid communication between said first and second convection zones; and 12. Apparatus according to claim 11 in which the convection-free capillary system has a very great resistance to flow, said transferring means includes a liquid pump for the transport of liquid from one homogenized portion to the other, and one of said fluid paths is formed by a liquid duct of high electric resistance for automatic reflux from the latter homogenized portion to the former.

13. Apparatus according to claim 11, in which the convection-free capillary system has a small resistance to flow, said means for homogenizing includes two fast circulation pumps for homogenization of two portions of the electrolytic conductor and said transferring means includes a liquid commutator in the form of a two-way stop-cock with two plug channels, serving the two liquid flows, and a mechanical device for regular exchange of the functions of said channels.

14. Apparatus according to claim 11, wherein said convection-free capillary system comprises a number of cooled and homogenized compartments, separated by membranes essentially perpendicular to the direction of the current and permeable to the ampolytes to be separated, and said transferring means includes a pumping device for continuous exchange of liquid between two compartments in the apparatus.

15. Apparatus according to claim 11, wherein said convection-free capillary system comprises a horizontal, cooled and insulating plate suitable for application of a moistened layer of a capillary system in electrolytic connection and arranged between said first and second compartments.

16. Apparatus according to claim 11, wherein said first and second compartments are disposed at different vertical levels, said capillary system includes at least one vertical, cooled and insulating tube suitable for filling with a moistened capillary system of high resistance to flow and in electrolytic connection with said two compartments, and said transferring means includes a liquid pump for transporting liquid from the lower to the higher homogenized compartment and a tube through which the same quantity of liquid flows back again to the lower compartment.

* * * * *

UNITED STATES PATENT AND TRADEMARK OFFICE
CERTIFICATE OF CORRECTION

PATENT NO. : 4,217,193
DATED : August 12, 1980
INVENTOR(S) : Harry Rilbe

It is certified that error appears in the above-identified patent and that said Letters Patent are hereby corrected as shown below:

Under "[30] Foreign Application Priority Data"

delete "June 2, 1977" and insert --June 1, 1977--.

Signed and Sealed this

Twenty-fifth Day of November 1980

[SEAL]

*Attest:*

SIDNEY A. DIAMOND

*Attesting Officer*    *Commissioner of Patents and Trademarks*